United States Patent [19]

Parkinson

[11] 4,424,232

[45] Jan. 3, 1984

[54] TREATMENT OF HERPES SIMPLEX

[76] Inventor: Richard W. Parkinson, 863 S. Carterville Rd., Orem, Utah 84057

[21] Appl. No.: 379,737

[22] Filed: May 19, 1982

[51] Int. Cl.³ ........................................... A61K 31/335
[52] U.S. Cl. .................................... 424/279; 424/280; 424/319; 424/322
[58] Field of Search ................................ 424/319, 279

[56] References Cited

U.S. PATENT DOCUMENTS

| | | | |
|---|---|---|---|
| 4,117,120 | 9/1978 | Elderbaum | 424/195 |
| 4,147,803 | 4/1979 | Ascucai et al. | 424/320 |
| 4,285,934 | 8/1981 | Tinnell | 424/148 |

OTHER PUBLICATIONS

Cumulated Index Medicus, vol. 21, 1980, p. 9297.

Primary Examiner—Leonard Schenkman
Attorney, Agent, or Firm—Terry M. Crellin

[57] ABSTRACT

Herpes simplex, cold sores, lesions, warts, blisters, burns, ulcers, and other painful skin conditions are treated by topical application of a composition comprising L-lysine, gibberellic acid, and urea in an inert carrier comprising water. The composition can additionally contain L-ascorbic acid, and a member selected from the group consisting of methyl paraben, propyl paraben, and mixtures thereof.

10 Claims, No Drawings

TREATMENT OF HERPES SIMPLEX

BACKGROUND OF THE INVENTION

1. Field

The invention relates to medical treatment of herpes simplex infections, burns, ulcers and other painful skin conditions by topical application of a medicant composition.

2. State of the Art

Herpes simplex is an infection by herpes simplex virus which is marked by the eruption of one or more groups of vesicles or sores on the human body, especially on the vermillion border of the lips, at the external nares, on the glans, prepuce, or vulva. The infection is commonly recrudescent and reappears during other febrile illness or even physiological states such as menstruation and high stress. The infection has also been called, according to its site, fever blisters, cold sores, herpes catarrhalis, herpes facialis, herpes febrilis, herpes genitalis, herpes labialis, herpes mentalis, herpes preputialis, and herpes progenitalis, Herpes simplex virus type 1 is known as the "skin" or "above the umbilicus" virus and type 2 is know as the "genital" or "below the umbilicus" virus. The two types cannot be distinguished in a culture, but can be distinguished on the basis of the antibodies generated upon exposure to the virus. The two types cross react with one another in the laboratory and are, thus, very closely related to each other.

Various treatments of herpes simplex have been proposed. U.S. Pat. No. 4,147,803 discloses the topical application of lauric diethanolamide to the area affected. Application of a mixture of boric acid, tannic acid, and salicylic acid is taught in U.S. Pat. No. 4,285,934. The use of lignosulfonate as a topical treating agent is disclosed in U.S. Pat. No. 4,185,097, and the application of kelp to the affected area is proposed in U.S. Pat. No. 4,117,120.

OBJECTIVE

The principal objective of the present invention is to provide a new method of treating herpes simplex and other painful skin conditions such as burns and ulcers by topical administration of a medication which has good activity against herpes simplex and which further acts very quickly to effect essentially total relief of pain from the affected area. This and other objects and advantages of the invention will become apparent from the following description.

DESCRIPTION OF THE INVENTION

It has been found that herpes simplex infections can be effectively combated by topical application to the affected area of an effective amount of a composition comprising L-lysine, gibberellic acid and urea. The active ingredients are preferably contained in a pharmaceutically inert carrier comprising water. In addition to the active ingredients mentioned above the composition may contain L-ascorbic acid, and a member selected from the group consisting of methyl paraben, propyl paraben or mixtures thereof. Ascorbic acid is known to be a healing agent for wounds and tissue repair. The methyl paraben and propyl paraben are used as a preservative for the active ingredients in the composition.

The composition of this invention contains, on a weight basis, from about 2 to 30% L-lysine, about 10 to 10,000 parts per million gibberellic acid, about 0.5 to 20% urea, with the balance being a pharmaceutically inert carrier comprising water. The carrier can be essentially clear, clean water, such as potable tapwater.

When the additional ingredients as mentioned above are included in the composition, they are present in an amount by weight from about 10 to 1,000 parts per million of L-ascorbic acid and from about 10 to 20,000 parts per million of the member selected from the group of methyl paraben, propyl paraben and mixtures thereof.

In a preferred composition, the active ingredients are contained in the composition in an amount, by weight, of from about 5 to 15% L-lysine, from about 100 to 1,000 parts per million gibberellic acid, and from about 1 to 5% urea. The additional ingredients can then be incorporated into the preferred composition in the amounts given above if so desired. When the term "parts per million" is used throughout the specification and claims, the indicated ingredient is to be present in the stated parts by weight per million parts by weight of the total composition.

The treatment of the herpes simplex infection or other painful skin condition in accordance with this invention comprises topical application of the composition disclosed herein to the affected area on the person suffering from the infection. An effective amount of the composition is applied to the affected area 4 to 6 times a day until healing is effected. Generally, complete healing, i.e., disappearance of symptoms including lesions, will be achieved within about 4 to 10 days. The total relief of pain from the affected area will be achieved within several hours, generally from about 4 to 24 depending upon the median size of the lesions when treatment is started.

The composition in accordance with the present invention is effective in the treatment of areas on the human body affected with herpes simplex virus, cold sores, lesions, warts (berrucae vulgaris) and blisters. The composition has also been found to be effective in treatment of burns, ulcers, and other painful skin conditions, bringing very quick relief from the pain experienced by such conditions as well as an aid in healing of the condition.

A composition consisting of, by weight, 10% L-lysine, 0.05% gibberellic acid, 2% urea, from 0.5 to 1% L-ascorbic acid, 1 to 2% methyl paraben and propyl paraben combined, and the balance essentially clear, clean water was used to treat 120 individuals suffering from herpes simplex labialis. The composition was applied topically to the affected areas so as to cover the affected areas with a coating of the composition about 4 to 6 times a day. The time from initiation of the symptoms and treatment with the composition to complete healing, i.e., disappearance of symptoms including lesions, averaged between about 122 hours and 206 hours. The time from the initiation of the treatment to when the patients experienced essentially complete relief of pain from the affected area averaged between about 12 hours and 18 hours.

In a control group of 40 individuals suffering from herpes simplex labialis, the infections were untreated. The individuals natural body mechanisms resulted in complete healing in an average of about 240 hours to 292 hours. The time from initiation of the symptoms to when the patients experienced essentially complete relief of pain from the affected area averaged between about 132 hours and 186 hours.

In another control group of 40 individuals suffering from herpes simplex labialis, the infections were treated with a composition containing only the inactive ingredients of the present invention, i.e., the L-ascorbic acid and the mixture of methyl and propyl paraben in the same concentration as in the composition containing the active compositions as used in the first tests reported above. The composition containing the inactive ingredients was applied topically to the affected areas so as to cover the affected areas with a coating of the composition about 4 to 6 times a day. The time from initiation of the symptoms and treatment with the composition containing only the inactive ingredients to complete healing averaged between about 246 hours and 268 hours. The time from the initiation of the treatment to when the patients experienced essentially complete relief of pain from the affected area averaged between about 128 hours and 170 hours.

In yet another control group of 40 individuals suffering from herpes simplex labialis, the infections were treated by topically applying a coating of an aqueous solution containing 10% L-lysine to the affected areas about 4 to 6 times a day. The time from initiation of the symptoms and treatment with the L-lysine solution to complete healing averaged between about 208 hours and 238 hours. The time from the initiation of the treatment to when the patients experienced essentially complete relief of pain from the affected area averaged between about 118 hours and 132 hours.

In still a further control group of 40 individuals suffering from herpes simplex labialis, the infections were treated by topically applying a coating of a composition containing gibberellic acid and urea in an inactive base about 4 to 6 times a day. The composition contained, on a weight basis, 0.05% gibberellic acid, 2% urea, from 0.5 to 1% L-ascorbic acid, 1 to 2% methyl paraben and propyl paraben combined, the balance being essentially clear, clean water. The time from initiation of the symptoms and treatment with the above composition to complete healing averaged between about 192 hours and 236 hours. The time from the initiation of the treatment to when the patients experienced essentially complete relief of pain from the affected area averaged between about 84 hours and 116 hours.

As can be seen, the combination of active ingredients in accordance with the invention results in reducing the average time for complete healing to about ½ the average time for complete healing of untreated infections. At least if not more significant, treatment with the composition of this invention results in complete relief of pain from the affected area in about 1/10 the time for such relief in untreated infections.

The control testing as reported above clearly shows that treatment with the inactive ingredients only was roughly equivalent to no treatment at all. The results achieved by treatment with L-lysine only or by treatment with the other active ingredients in the absence of L-lysine were of several magnitudes less effective, especially in the time for relief of pain from the affected area, than by treatment in accordance with the invention. Only when the active ingredients were combined in accordance with the present invention were the significant reduction in time to heal and the dramatic reduction in time to relief of pain achieved.

Similar testing has shown that the compositions of the present invention are effective within the broad range of concentrations recited herein. The preferred range of concentrations result in economic and practical advantages. Loss of effectiveness occurs when concentrations below the lower limits recited herein are used.

Although preferred embodiments of the invention have been disclosed, it is to be understood that various changes and modifications can be made without departing from the subject matter coming within the scope of the following claims, which subject matter I regard as my invention.

I claim:

1. A method of treating herpes simplex comprising topically applying to the area affected an effective amount of a composition comprising from about 2% to 30% by weight L-lysine, from about 10 to 10,000 parts per million by weight gibberellic acid, and from about 0.5% to 20% by weight urea in an inert carrier comprising water.

2. A method as claimed in claim 1, wherein the composition further comprises from about 10 to 1,000 parts per million by weight L-ascorbic acid.

3. A method as claimed in claim 1, wherein the composition contains from about 5 to 15% L-lysine, from about 100 to 1,000 parts per million gibberellic acid, and from about 1 to 5% urea.

4. A method as claimed in claim 1, wherein the composition further contains from about 10 to 20,000 parts per million by weight of a member selected from the group consisting of methyl paraben, propyl paraben and mixtures thereof.

5. A method as claimed in claim 1, wherein the composition further comprises from about 10 to 1,000 parts per million by weight L-ascorbic acid, and from about 10 to 20,000 parts per million by weight of a member selected from the group consisting of methyl paraben, propyl paraben, and mixtures thereof.

6. A method as claimed in claim 5, wherein the composition contains from about 5 to 15% L-lysine, from about 100 to 1,000 parts per million gibberellic acid, and from about 1 to 5% urea.

7. A composition for topical application to areas on the human body affected with herpes simplex virus, said composition comprising from about 2% to 30% by weight L-lysine, from about 10 to 10,000 parts per million by weight gibberellic acid, and from about 0.5% to 0.20% by weight urea in an inert carrier comprising water.

8. A composition as claimed in claim 7 further comprising from about 10 to 1,000 parts per million by weight L-ascorbic acid.

9. A composition as claimed in claim 7 comprising from about 5 to 15% L-lysine, from about 100 to 1,000 parts per million gibberelic acid, and from about 1 to 5% urea.

10. A composition as claimed in claim 7 further comprising from about 10 to 1,000 parts per million by weight L-ascorbic acid, and from about 10 to 20,000 parts per million by weight of a member selected from the group consisting of methyl paraben, propyl paraben, and mixtures thereof.

* * * * *